_United States Patent_ [19]

Georgiev et al.

[11] Patent Number: 4,732,909

[45] Date of Patent: Mar. 22, 1988

[54] 3-(3-HALOPHENYL-3,4-DIAZATETRACYCLO-[6.3.1.1$^{6,10}$.0$^{1,5}$]TRIDEC-4-EN-2-ONE COMPOUNDS AND USE THEREOF TO TREAT HYPOXIA

[75] Inventors: Vassil S. Georgiev, Penfield; George B. Mullen, Avon; Patricia A. Swift, Rochester, all of N.Y.

[73] Assignee: Pennwalt Corporation, Philadelphia, Pa.

[21] Appl. No.: 61,068

[22] Filed: Jun. 10, 1987

[51] Int. Cl.$^4$ .................. A61K 31/415; C07D 231/54
[52] U.S. Cl. ..................................... 514/404; 548/359
[58] Field of Search .......................... 548/359; 514/404

[56] References Cited

PUBLICATIONS

Stetter et al., "1,2 Diamines of Adamantane, Homoadamantane and Noradamantane" (German, with English abstract) *Justus Liebigs Ann. Chem.*, (6) 999–1004 (1977).

Armarego et al., "The Synthesis of 3.5 Diazatetracyclo[7.3.1.1$^{7,11}$0$^{1,6}$]-tetradecanes" *Aust. J. Chem.*, vol. 31, 1769–1775 (1978).

Moiseev et al., "Admantane and its Derivatives: 1.Hydrazones and Pyrazolones of Adamantane" *Khim. Geterotskil. Soedin.*, (4), 528–531 (1982).

*Primary Examiner*—Henry R. Jiles
*Assistant Examiner*—Kurt G. Briscoe
*Attorney, Agent, or Firm*—Seidel, Gonda, Goldhammer & Abbott

[57] ABSTRACT

3-(3-Halophenyl)-3,4-diazatetracyclo-[6.3.1.1$^{6,10}$.0$^{1,5}$]tridec-4-en-2-ones are useful as antihypoxia agents.

4 Claims, No Drawings

3-(3-HALOPHENYL-3,4-DIAZATETRACYCLO-[6.3.1.1^{6,10}.0^{1,5}]TRIDEC-4-EN-2-ONE COMPOUNDS AND USE THEREOF TO TREAT HYPOXIA

BACKGROUND OF THE INVENTION

The invention relates to 3-(3-halophenyl)-3,4-diazatetracyclo[6.3.1.1$^{6,10}$.0$^{1,5}$]tridec-4-en-2-ones, which possess antihypoxia activity.

3,4-Diazatetracyclo[6.3.1.1$^{6,10}$.0$^{1,5}$]tridec-4-en-2-one is disclosed in the following references: Stetter et al., *Justus Liebigs Ann. Chem.*, (6) 999–1004 (1977); Armarego et al., *Aust. J. Chem.*, Vol. 31, 1769–75 (1978); and Moiseev et al., *Khim. Geterotsikl. Soedin.* (4), 528–531 (1982). Moiseev et al. further disclose 3-(3-phenyl)-3,4-diazatetracyclo[6.3.1.1$^{6,10}$.0$^{1,5}$]tridec-4-en-2-one.

None of the references teach the compounds of the present invention.

SUMMARY OF THE INVENTION

The invention provides compounds of the formula:

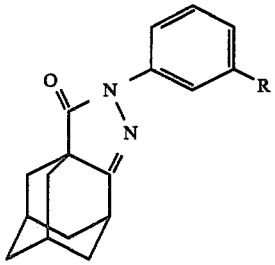

(1)

wherein R is a halogen, preferably chlorine.

The invention also provides a method for treating a warm-blooded animal for hypoxia, which comprises administering to such animal an effective amount of a compound of formula 1.

DETAILED DESCRIPTION OF THE INVENTION 3-(3-Halophenyl)-3,4-diazatetracyclo[6.3.1.1$^{6,10}$.0$^{1,5}$]-tridec-4-en-2-ones may be prepared by reacting 1-adamantanol (2) with lead tetracetate and iodine according to the procedure of Majerski and Hamersak, *Org. Syn.*, Vol. 59, 147 (1980). The resulting protoadamantanone (3) is converted into the 2-oxoadamantane-1-carboxylic acid (4) via the procedure of Chakrabarty et al., *J. Chem. Soc.*, (Perkin Trans. I) 1893–1900 (1976). Compound 4 is esterified, and the ethyl ester derivative 5 is reacted with a 3-halophenylhydrazine hydrochloride to provide, for example, 3-(3-chlorophenyl)-3,4-diazatetracyclo[6.3.1.1$^{6,10}$.0$^{1,5}$]tridec-4-en-2-one (6).

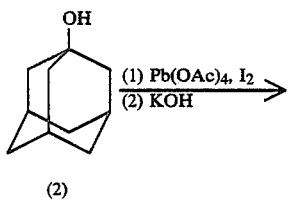

The following procedures describe the preparation of the starting material and intermediates utilized in the preparation of the 3-(3-halophenyl)-3,4-diazatetracyclo[6.3.1.1$^{6,10}$.0$^{1,5}$]tridec-4-en-2-ones. All temperatures are centigrade unless indicated otherwise.

PREPARATION 1

Protoadamantan-4-one (3)

The title compound is prepared according to the following method of Majerski et al., *Org. Syn.* Vol. 59, 147–148 (1978).

A 2-l., three-necked, round-bottomed flask equipped with an efficient mechanical stirrer and a reflux condenser is charged with 600 ml of dry benzene. The flask is immersed in a water bath, stirring is initiated, and 58.3 g (0.132 mol) of lead tetraacetate, 37.4 g (0.147 mol) of iodine, and 10.0 g. (0.066 mol) of 1-adamantanol are added. The bath temperature is gradually raised to 80° over a 20-minute period and is then allowed to cool to 70°–75°. Stirring is continued for 2 hours at 70°–75° and for an additional hour while the mixture is cooled to room temperature. The temperature of the bath should be carefully maintained in this range. The inorganic salts are filtered and carefully washed with five 50-ml portions of ethyl ether. The benzene filtrate and ether washings are combined in a 2-l. separatory funnel and shaken with 500 ml of saturated aqueous sodium bisulfite until the dark red color disappears. The layers are *not* separated. If the color reappears within 10–15 minutes, the mixture is shaken again until colorless. This procedure is repeated as many times as necessary. The layers are then separated, and the organic layer is washed with 500 ml of water and 250 ml of saturated aqueous sodium bicarbonate. The benzene-ether solution is dried over anhydrous magnesium sulfate for 1 hour and concentrated in a 500-ml, round-bottomed flask with a rotary evaporator. The flask containing the resulting crude iodo ketone is equipped with a magnetic stirring bar and a reflux condenser. A solution of 7 g (0.125 mol) of potassium hydroxide in 150 ml of methanol is added, and the mixture is stirred and heated at reflux for 3 hours. The contents of the flask are allowed to cool to room temperature and poured into 300 ml of ice-water. The resulting mixture is extracted with five 100-ml portions of ether. The combined extracts are dried over anhydrous magnesium sulfate and evaporated under reduced pressure, leaving 8.6–9.1 g of a yellow solid. A solution of this crude product in 3 ml of chloroform is allowed to percolate onto a chromatography column packed with 200 g of activity III, neutral alumina in pentane. (Activity III alumina may be prepared by adding 6% (w/w) of water to neutral alumina of activity grade I). The column is eluted first with 100 ml of pentane and then with 500 ml of 3:7 (v/v) ether-pentane as 25-ml fractions are collected and analyzed by gas chromatography. (1.5 m×3.2 mm column packed with 10% diethylene glycol succinate supported on 60/80 mesh Chromosorb W and heated at 140° C.). Those fractions containing product whose purity is judged to be 98% or greater are combined and evaporated, affording 7.0–8.1 g (71–82% based on 1-adamantanol) of protoadamantan-4-one (3) as a colorless or pale yellow solid, m.p. 202°–204°.

PREPARATION 2

2-Oxoadamantane-1-carboxylic Acid (4)

The following procedure of Chakrabarti et al, *J. Chem. Soc.*, (Perkin Trans. I) 1983–1900 (1976) is used to convert protoadamantan-4-one to the intermediate protoadamantane-4-spiro-oxiran, which is then converted to the title compound by Jones oxidation.

To a solution of protoadamantan-4-one (15.1 g, 0.1 mol) and trimethylsulphonium iodide (31 g, 0.15 mol) in dry dimethyl sulphoxide (200 ml) is added potassium t-butoxide (14 g) under a stream of nitrogen (the outlet is connected to a trap containing chromic acid to destroy the dimethyl sulphide formed). The mixture is stirred at 50°–55° for 18 h, cooled to ca. 10° and poured into ice-water (200 ml). The product is extracted with carbon tetrachloride and the extract is washed with water, dried and evaporated under vacuum to give an oil (16.3 g), which is distilled at 70°–80° C. and 1.5 mm Hg to yield protoadamantane-4-spirooxiran as a white waxy solid (12.8 g), m.p. 62°–64°.

To a stirred solution of the latter, (2.0 g, 0.012 mol) in reagent grade acetone (200 ml), Jones reagent (50 ml of a solution containing 13.4 g chromic oxide and 11.5 ml concentrated sulphuric acid) is added dropwise over 20 min. The mixture is stirred for 2 h and then methanol (50 ml) is added to destroy the excess of oxidant; the mixture is then diluted with water, and extracted with chloroform. The organic phase is washed with water, dried, and evaporated to a white semi-solid. Crystallization from carbon tetrachloride gives the pure product (1.4 g), 2-oxoadamantane-1-carboxylic acid (4), m.p. 167°–169°.

PREPARATION 3

Ethyl 2-Oxoadamantane-1-carboxylate (5)

A solution of 2-oxoadamantane-1-carboxylic acid (4) (2.06 g, 10.6 mmol) in 20 ml of thionyl chloride is refluxed for 2 hours. The solution is then cooled to room temperature and the excess thionyl chloride is removed under reduced pressure. The oily residue is dissolved in 10 ml of ether and added to a solution of 2 ml of triethylamine in 25 ml of ethanol at 0°. The resulting solution is stirred for 30 min, then diluted with 100 ml of ice-water and extracted with 200 ml of ether. The organic layer is dried over anhydrous magnesium sulfate and flash-chromatographed over silica gel using ethyl acetate as the eluent. Ethyl 2-oxoadamantane-1-carboxylate (5) is obtained as an oily material (1.56 g, 71%).

The compounds of the invention may be prepared by reacting ethyl 2-oxoadamantane-1-carboxylate (5) with a 3-halophenylhydrazine according to the following example:

EXAMPLE 3-(3-Chlorophenyl)-3,4-diazatetracyclo[$6.3.1.1^{6,10}.0^{1,5}$]-tridec-4-en-2-one (6)

To a solution of ethyl 2-oxoadamantane-1-carboxylate (5) (1.0 g, 4.5 mmol) and 3-chlorophenylhydrazine hydrochloride (3.6 g, 20 mmol) in 40 ml of ethanol is added triethylamine (2.0 g, 20 mmol). The reaction mixture is stirred at room temperature under a nitrogen atmosphere for 20 hours, then heated to reflux for 2 hours. After cooling to ambient temperature, the solvent is removed under reduced pressure and the crude residue solid is dissolved in 30 ml of methylene chloride. The organic extract is washed with 25 ml of diluted hydrochloric acid to remove the excess of 3-chlorophenylhydrazine, then dried over anhydrous magnesium sulfate. The solvent is evaporated to leave the title compound (6) as a dark-colored, viscous oil which is flash-chromatographed on silica gel using ether-pentane (2:8) as the eluent. Subsequent recrystallization from methanol provides the pure product as pale yellow needles melting at 119.5°–120.5° C. Anal. Calcd for $C_{17}H_{17}ClN_2O$: C, 67.88; H, 5.70; N, 9:31; Cl, 11.79. Found: C, 67.54; H, 5.75; N, 9.12; Cl, 11.86.

The compounds of the invention possess antihypoxia activity as observed in mice when administered by intraperitoneal injection.

The antihypoxia test measures the survival duration of mice in a normobaric atmosphere consisting of 96% nitrogen and 4% oxygen, at ambient temperature. The mice are considered dead when they stop visible aspiration. The test indicates potential clinical utility in situations of central nervous system hypoxia, such as occurs following stroke, cardiac arrest, and traumatic accidents.

As observed from the Table, 3-(3-chlorophenyl)-3,4-diazatetracyclo[$6.3.1.1^{6,10}.0^{1,5}$]tridec-4-en-2-one, when administered intraperitoneally at a dose of 25 mg/kg, prolonged the survival of mice by a very significant margin. The quantity "P" in the Table denotes statistical significance.

TABLE

| Minimal Neurotoxic Dose (mg/kp, ip) | Estimated $LD_{50}$ (mg/kg, ip) | Antihypoxia | | | | | | |
|---|---|---|---|---|---|---|---|---|
| | | Dose (mg/kg) | Route | $N^1$ | Temp. | Surval Minutes | | P |
| | | | | | | Control | Compound | |
| 25 | >100 | 25 | ip | 5 | ambient | 8.7 | 13.0 | 0.075 |

TABLE-continued

| Minimal Neurotoxic Dose (mg/kp, ip) | Estimated LD$_{50}$ (mg/kg, ip) | Antihypoxia | | | | | | |
|---|---|---|---|---|---|---|---|---|
| | | Dose (mg/kg) | Route | N$^1$ | Temp. | Survival Minutes | | |
| | | | | | | Control | Compound | P |
| | | 2.5 | ip | 10 | ambient | 8.7 | 8.0 | NS |
| | | 5 | ip | 10 | ambient | 8.7 | 10.5 | <0.05 |
| | | 10 | ip | 10 | ambient | 6.9 | 9.5 | <0.05 |
| | | 25 | ip | 10 | ambient | 6.9 | 12.6 | <0.05 |

N$^1$ = Number of mice in each group
NS = Not significant (P > 0.05)
ip = intraperitoneal administration The compounds of the invention may be administered parenterally in a pharmaceutically acceptable carrier.

The present invention may be embodied in other specific forms without departing from the spirit or essential attributes thereof and, accordingly, reference should be made to the appended claims, rather than to the foregoing specification, as indicating the scope of the invention.

We claim:

1. A compound having the formula:

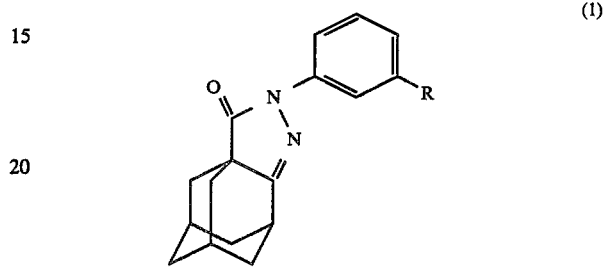

wherein R is a halogen.

2. A compound according to claim 1 wherein R is chlorine.

3. A method for treating a warm-blooded animal for hypoxia which comprises administering to such animal an effective amount of a compound of claim 1.

4. A method according to claim 3 wherein the compount is 3-(3-chlorophenyl)-3,4-diazatetracyclo[6.3.1.1$^{6,10}$.0$^{1,5}$]tridec-4-en-2-one.

* * * * *